United States Patent [19]

Wilson

[11] Patent Number: 4,546,087

[45] Date of Patent: Oct. 8, 1985

[54] METHOD FOR DETECTING THE PRESENCE OF A CHROMATE COATING ON ALUMINUM

[75] Inventor: Lance K. Wilson, Waterloo, Iowa

[73] Assignee: Deere & Company, Moline, Ill.

[21] Appl. No.: 437,702

[22] Filed: Oct. 29, 1982

[51] Int. Cl.$^4$ ..................... G01N 21/78; G01N 33/18
[52] U.S. Cl. .......................................... 436/5; 436/83
[58] Field of Search ............... 436/5, 83, 84; 423/595; 73/104; 356/402

[56] References Cited

U.S. PATENT DOCUMENTS

| | | | |
|---|---|---|---|
| 2,902,348 | 9/1959 | Ostrander | 436/5 |
| 4,244,693 | 1/1981 | Guon | 436/5 |
| 4,287,002 | 9/1981 | Torok | 134/36 |
| 4,327,134 | 4/1982 | Baldi | 156/665 |
| 4,383,042 | 5/1983 | Coggins et al. | 436/5 |

OTHER PUBLICATIONS

*Spot Tests* by Fritz Feigl, vol. I, Inorganic Applications 1954, pp. 314–337, Elsevier Publishing Co.

*Primary Examiner*—Arnold Turk

[57] ABSTRACT

A method is disclosed for detecting the presence of a chromate coating on the surface of aluminum. The method includes the application of a few milliliters of a liquid composition to the surface of the aluminum. The liquid composition includes one part of potassium permanganate having a concentration of at least 0.5 weight/volume percent and one part of concentrated sodium hydroxide saturated in an aqueous solution. The liquid has a beet-red pigmentation which undergoes a color change to a bright blue-green pigmentation when it reacts with a chromate coating. If no coating is present on the aluminum surface, the liquid will react with the aluminum and the alloys contained therein to produce a beige color.

4 Claims, No Drawings

METHOD FOR DETECTING THE PRESENCE OF A CHROMATE COATING ON ALUMINUM

FIELD OF THE INVENTION

The present invention relates to a method for the detection of the presence of a chromate coating on the surface of aluminum.

BACKGROUND OF THE INVENTION

Currently, many engine blocks and engine parts are made of aluminum to provide a lighter weight vehicle. When using aluminum, it is necessary to treat the surface with chromic acid to remove oxides so as to improve paint adherence. In so doing, a very faint light gold appearance is obtained on the aluminum part. However, in today's modern factories, wherein sodium vapor lights are used, it is sometimes very difficult for a person to visually detect the presence of a chromate coating. Up until now, the presence of such a coating could only be positively identified by a very time consuming analysis of atomic absorption. Therefore, there is a desire in the industry to provide a fast, on-the-spot and reliable means of detecting the presence of a chromate coating on aluminum parts which are to be painted.

Now a method and composition have been invented for detecting such a coating.

SUMMARY OF THE INVENTION

Briefly, this invention relates to a method for detecting the presence of a chromate coating on an aluminum surface. The method includes the application of a few milliliters of a liquid solution comprising one part of potassium permanganate having a concentration of at least 0.5 percent weight per volume (0.5 grams of $KMnO_4$ per 100 milliliters of $H_2O$) and one part of concentrated sodium hydroxide. The liquid solution has a beet-red pigmentation and reacts on the aluminum surface such that a color change will be produced. During the color change, the solution will change from a beet-red pigmentation to a bright blue-green pigmentation when a chromate coating is present and will change from a beet-red pigmentation to a beige color if no chromate coating is present.

The general object of this invention is to provide a method for detecting the presence of a chromate coating on the surface of aluminum. A more specific object of this invention is to provide a fast, on-the-spot and reliable test for detecting a chromate coating on an aluminum surface.

Another object of this invention is to provide a simple and inexpensive method of detecting the presence of a chromate coating on the surface of aluminum.

Still further, an object of this invention is to provide a composition of matter which is useful in detecting the presence of a chromate coating on the surface of aluminum by visually changing colors.

Other objects and advantages of the present invention will become more apparent to those skilled in the art in view of the following description.

DETAILED DESCRIPTION OF THE INVENTION

In accordance with this invention, a liquid composition is prepared for use in detecting the presence of a chromate coating on the surface of an aluminum part, such as the aluminum block of an engine. The liquid composition is made up of one part of potassium permanganate having a concentration of at least 0.5 weight per volume percent and one part of concentrated sodium hydroxide. Preferably, the concentration of the potassium permanganate is between 0.5 and 1.0 weight per volume percent (0.5 and 1.0 grams of $KMnO_4$ per 100 milliliters of water) and the concentrated sodium hydroxide is a saturated aqueous solution.

The method for detecting the presence of a chromate coating on the surface of aluminum includes the steps of applying a couple of drops of the aforementioned liquid composition to a level surface of the aluminum part. The liquid will have a beet-red pigmentation since potassium permanganate is beet-red in color while concentrated sodium hydroxide is clear in color. The clear sodium hydroxide does not change the beet-red pigmentation of the potassium permanganate when the two are combined. Although equal amounts of the potassium permanganate and the sodium hydroxide can be combined to form the liquid composition, it should be noted that best results are obtained when the sodium hydroxide exceeds the potassium permanganate and preferably the ratio is three parts of sodium hydroxide to two parts of potassium permanganate. The presence of a greater amount of sodium hydroxide with the potassium permanganate speeds up the reaction. When the liquid composition is applied to a surface of aluminum having a chromate coating, the liquid composition will react with the coating to produce a color change in which the beet-red pigmentation will change to a bright blue-green pigmentation. If no chromate conversion is present, the liquid composition will react with the aluminum and the alloys contained therein to form a dull brown or beige color. It should be noted that the concentrated sodium hydroxide is very caustic and acts as a catalyst to allow the reaction to progress between the aluminum and the potassium permanganate.

As explained above, a liquid composition comprising equal parts of potassium permanganate and concentrated aqueous sodium hydroxide can be applied to an aluminum part to detect the presence of a chromate coating. However, by experimentation, it has been found that by first applying 0.1 milliliter of potassium permanganate having a concentration of at least 0.5 percent to an aluminum surface and then applying 0.15 milliliter of concentrated sodium hydroxide to the potassium permanganate that the method also works. Within a short period of time, approximately 30 to 60 seconds, the liquid composition will react with the aluminum surface and a color change will occur. The colors will be the same as explained above. Likewise, the method for detecting the presence of a chromate coating on an aluminum surface will work if the sodium hydroxide is first applied to the aluminum surface and then the potassium permanganate is combined with it.

The following example is set forth to further illustrate the advantages and utility of the present invention.

EXAMPLE

The following method was used to detect the presence or nonpresence of a chromate coating on several specimens of aluminum parts, some of which contained a chromate coating and some of which did not. Visually, one could not distinguish the parts apart. First, approximately 0.1 milliliter of potassium permanganate, having a concentration of between 0.5-1.0 weight/volume percent was applied to a small surface area on the aluminum parts. Immediately thereafter, 0.15 milliliter of concentrated sodium hydroxide saturated in an aqueous solution was applied to the potassium permanganate. The combined liquid composition had a beet-red color. Approximately 30 to 60 seconds after the solution was applied to the aluminum surfaces which contained a chromate coating, the color changed from beet-red to a bright blue-green. Tests conducted on aluminum parts that did not have a chromate coating resulted in a color change from beet-red to beige or dull brown. The beige or dull brown indicated that the liquid composition had reacted with the aluminum and the alloys contained therein.

While the particular details set forth above are capable of attaining the objects and providing the advantages herein stated, the specific materials described and the method disclosed are merely illustrated and could be varied through the use of other oxidizers and catalysts. Accordingly, this invention is intended to embrace all techniques which produce the same results without departing from the scope of the inventive concept as defined in the appended claims.

I claim:

1. A method for detecting the presence of a chromate coating on the surface of an aluminum part, said method comprising applying to the surface of said aluminum part a few milliliters of a liquid composition comprising from one to two parts of an aqueous solution of potassium permanganate having a concentration of at least 0.5 weight/volume percent with one to three parts of a concentrated sodium hydroxide solution, said liquid composition having a beet-red pigmentation, whereby any chromate coating present on the surface of said aluminum part will react with said liquid composition to produce a color change to a bright blue-green pigmentation.

2. A method for detecting the presence of a chromate coating on the surface of an aluminum part, said method comprising applying at least two parts of an aqueous solution of potassium permanganate having a concentration of between 0.5-1.0 weight/volume percent and at least three parts of concentrated sodium hydroxide to the surface of said aluminum part, said mixture of potassium permanganate and sodium hydroxide forming a liquid composition having a beet-red color, whereby any chromate coating present on the surface of said aluminum part will react with said liquid composition to produce a color change to a bright blue-green pigmentation.

3. A method for detecting the presence of a chromate coating on the surface of an aluminum part, said method comprising the steps of:
   (a) applying about 0.1 ml of an aqueous solution of potassium permanganate having a concentration of at least 0.5 weight/volume percent to the surface of said aluminum part;
   (b) applying about 0.1 to 0.15 ml of a concentrated sodium hydroxide solution to said potassium permanganate to form a liquid composition having a beet-red color; and
   (c) permitting said liquid composition to react on the surface of said aluminum part until a color change has occurred whereby a change in color from beet-red to a bright blue-green indicates the presence of a chromate coating and a change in color from beet-red to beige indicates the non-presence of a chromate coating.

4. A method for detecting the presence of a chromate coating on the surface of an aluminum part, said method comprising the steps of:
   (a) applying about 0.10 to 0.15 ml of a concentrated sodium hydroxide solution to the surface of said aluminum part;
   (b) applying about 0.1 ml of an aqueous solution of potassium permanganate having a concentration of at least 0.5 weight/volume percent to said concentrated sodium hydroxide to form a solution having a beet-red color; and
   (c) permitting said liquid composition to react on the surface of said aluminum part until a color change has occurred whereby a change in color from beet-red to a bright blue-green indicates the presence of a chromate coating and a change in color from beet-red to beige indicates the non-presence of a chromate coating.

* * * * *